United States Patent [19]

Minami et al.

[11] 4,110,537
[45] Aug. 29, 1978

[54] METHOD OF PRODUCING N[1]-(2-TETRAHYDROFURYL)-5-FLUOROURACIL

[75] Inventors: Isao Minami, Suita; Yoshio Yoshioka; Hiroaki Nomura, both of Takatsuki, all of Japan

[73] Assignee: Takeda Chemical Industries, Ltd., Osaka, Japan

[21] Appl. No.: 751,541

[22] Filed: Dec. 16, 1976

[30] Foreign Application Priority Data

Dec. 25, 1975 [JP] Japan .................................. 50-156800

[51] Int. Cl.$^2$ ............................................ C07D 405/04
[52] U.S. Cl. ..................................................... 544/313
[58] Field of Search ......................................... 260/260

[56] References Cited
PUBLICATIONS

Brossmer et al., Chemical Abstracts, vol. 78 (1973), 58343r.

Primary Examiner—Paul M. Coughlan, Jr.
Attorney, Agent, or Firm—Burgess, Ryan and Wayne

[57] ABSTRACT

N[1]-(2-tetrahydrofuryl)-5-fluorouracil is produced in high yield by reacting 5-fluorouracil with 2,3-dihydrofuran in the presence of trimethylsilyl chloride and a tertiary amine and treating the resultant mixture with an aqueous alkaline solution.

9 Claims, No Drawings

METHOD OF PRODUCING N¹-(2-TETRAHYDROFURYL)-5-FLUOROURACIL

This invention relates to a new and useful method for producing $N^1$-(2-tetrahydrofuryl)-5-fluorouracil which is of value as a carcinostatic agent.

As a representative example of the prior art method for producing the aforementioned contemplated compound of the present invention, there is known the process described in Japanese Patent Publication No. 10510/1974, which comprises silylating 5-fluorouracil with trimethylsilyl chloride and reacting the resultant silyl derivative with 2-chlorotetrahydrofuran under cooling (about $-30°$ C.).

In the above known process, the reaction is carried out under cooling at about $-30°$ C. and it is known that the starting material 2-chlorotetrahydrofuran is chemically unstable, being ready to decompose rapidly even at low temperature.

2-Chlorotetrahydrofuran can be industrially prepared by causing hydrogen chloride to undergo addition to 2,3-dihydrofuran.

We studied the conditions of reaction that could be employed for the production of the aforementioned product compound starting with 2,3-dihydrofuran and 5-fluorouracil, and found unexpectedly that, in the presence of trimethylsilyl chloride and a tertiary amine, the reaction proceeds smoothly even at room temperature, that is to say, without the need of heating or cooling, giving rise to the desired compound in high yield. This invention has been accomplished based upon the above finding.

It is an object of the present invention to provide a simplified and economical method to produce $N^1$-(2-tetrahydrofuryl)-5-fluorouracil from 5-fluorouracil.

Another object of the invention is to provide a method for producing $N^1$-(2-tetrahydrofuryl)-5-fluorouracil by reacting 5-fluorouracil with 2,3-dihydrofuran in the presence of trimethylsilyl chloride and a tertiary amine and treating the resultant mixture with an aqueous alkaline solution.

The present invention is directed to a method of producing $N^1$-(2-tetrahydrofuryl)-5-fluorouracil characterized in that said method comprises reacting 5-fluorouracil with 2,3-dihydrofuran in the presence of trimethylsilyl chloride and a tertiary amine and treating the resultant mixture with an alkaline aqueous solution.

In accordance with this invention, 5-fluorouracil is reacted with 2,3-dihydrofuran in the presence of trimethylsilyl chloride and a tertiary amine. As said tertiary amine, there may be mentioned triethylamine, trimethylamine, N-methylmorpholine, dimethlaniline, N-methylpiperidine, pyridine and so forth.

Generally, this reaction may be conducted at about $0°-30°$ C., usually at room temperature, and in an anhydrous organic solvent, although it may be carried out under appropriate heating. As the solvent, there may be employed any of such aprotic anhydrous organic solvent such as dimethylformamide, acetonitrile, methylene chloride, 1,2-dichloroethane, pyridine, benzene, etc. or an appropriate mixture of such solvents. The staring materials may be used, for example in the following range of mole ratios. 5-Fluorouracil: 2,3-dihydrofuran: trimethylsilyl chloride: tertiary amine = 1: about 1.2 to 2.0: about 2: about 1.

The resulted reaction mixture is treated with an aqueous alkaline solution, for example, an aqueous solution of sodium hydrogen carbonate, sodium carbonate, sodium hydroxide or potassium hydroxide. By this treatment, pH of the mixture is adjusted to generally about 3 to about 8 and the silyl group is removed from the resultant product to yield the objective compound. Then the mixture is extracted with an organic solvent, for examle, chloroform. The extract is concentrated and the concentrate may be recrystallized or column-chromatographed to isolate and purify the desired product.

The method according to this invention has the following advantages over the aforementioned prior art method.

(1) Whereas the known method is practiced under cooling at $-30°$ C., the reaction of this invention can be conducted at room temperature.

(2) Inasmuch as the starting material 2-chlorotetrahydrofuran for the prior art method is produced by adding hydrogen chloride to 2,3-dihydrofuran, which is a starting material compound for this invention, the present method starting with 2,3-dihydrofuran involves fewer production steps and provides the desired product compound at less cost.

(3) The reaction procedure according to this invention is easier to follow because, whereas the starting material 2-chlorotetrahydrofuran for the prior art method is chemically unstable, the present invention employes the chemically stable compound, 2,3-dihydrofuran, as a starting material.

EXAMPLE

In 10 ml of dimethylformamide were dissolved 1.3 g of 5-fluorouracil together with 1.05 g of 2,3-dihydrofuran and 2.16 g of trimethylsilyl chloride. Following the addition of 1.01 g of triethylamine, the solution was stirred at room temperature for 20 hours. Then, it was rendered weakly alkaline with a 10% aqueous solution of sodium bicarbonate and the aqueous layer was washed with chloroform and rendered weakly acidic with 1N-hydrochloric acid.

It was then extracted three times with 20 ml portions of chloroform, dried over sodium sulfate and filitered. The filtrate was distilled to remove the solvent and the residue was recrystallized from ethanol. By the above procedure was obtained 1.4 g colorless needles of $N^1$-(2-tetrahydrofuryl)-5-fluorouracil. Melting point: 164–165° C. Elemental analysis ($C_8H_9N_2O_3F$)

|  | C | H | N |
|---|---|---|---|
| Found: | 47.90 | 4.58 | 13.92 |
| Calcd.: | 48.00 | 4.53 | 14.00 |

We claim:

1. A method for producing $N^1$-(2-tetrahydrofuryl)-5-fluorouracil which comprises reacting a ratio of 1 mol of 5-fluorouracil with about 1.2 to 2.0 mols of 2,3-dihydrofuran in the presence of about 2 mols of trimethylsilyl chloride and about 1 mol of a tertiary amine in an aprotic anhydrous organic solvent, and treating the resultant mixture with an aqueous alkaline solution.

2. A method according to claim 1 wherein said reaction is conducted at about 0°–30° C.

3. A method according to claim 2 wherein said reaction is conducted at room temperature.

4. A method according to claim 1, wherein said solvent is selected from the group consisting of dimethylformamide, acetonitrile, methylene chloride, 1,2-dichloroethane, pyridine, benzene, and mixture thereof.

5. A method according to claim 4 wherein said solvent is dimethylformamide.

6. A method according to claim 1 wherein said amine is selected from the group consisting of triethylamine, trimethylamine, N-methylmorpholine, dimethylaniline, N-methylpiperidine, and pyridine.

7. A method according to claim 6 wherein said amine is triethylamine.

8. A method according to claim 1 wherein the pH of said resultant mixture is adjusted to from about 3 to about 8 with said alkaline solution.

9. A method according to claim 8 wherein said alkaline solution is an aqueous solution of sodium bicarbonate, sodium carbonate, sodium hydroxide or potassium hydroxide.

* * * * *

UNITED STATES PATENT OFFICE
CERTIFICATE OF CORRECTION

Patent No. 4,110,537          Dated August 29, 1978

Inventor(s) Isao Minami, et al

It is certified that error appears in the above-identified patent and that said Letters Patent are hereby corrected as shown below:

Column 1, line 53: "dimethlaniline" should be --dimethylaniline-- line 63: "staring" should be --starting-- line 64: "5-Fluorouracil" should begin a new paragraph

Column 2, line 7 : "examle" should be --example--

Signed and Sealed this

Twenty-ninth Day of May 1979

[SEAL]

Attest:

RUTH C. MASON
Attesting Officer

DONALD W. BANNER
Commissioner of Patents and Trademarks